United States Patent [19]

Lehky

[11] 4,433,163

[45] Feb. 21, 1984

[54] PROCESS FOR THE PRODUCTION OF 3,3-DIMETHYLGLUTARIC ACID OR ITS ESTERS

[75] Inventor: Pavel Lehky, Naters, Switzerland

[73] Assignee: Lonza Ltd., Basel, Switzerland

[21] Appl. No.: 381,342

[22] Filed: May 24, 1982

[30] Foreign Application Priority Data

May 27, 1981 [CH] Switzerland ............... 3474/81

[51] Int. Cl.$^3$ ............... C07C 67/42; C07C 51/34
[52] U.S. Cl. ............... 560/204; 562/528; 562/590
[58] Field of Search ............... 560/204; 562/590, 528

[56] References Cited

U.S. PATENT DOCUMENTS

| | | | |
|---|---|---|---|
| 1,972,579 | 9/1934 | Wickert | 560/204 X |
| 1,974,917 | 9/1934 | Halbig et al. | 560/204 |
| 2,971,915 | 2/1961 | Borsoff et al. | 252/56 |
| 3,012,038 | 12/1961 | O'Neill et al. | 562/528 |
| 3,646,126 | 2/1972 | Richtzenhain et al. | 562/590 X |
| 4,158,739 | 6/1979 | Schulz et al. | 562/590 X |
| 4,322,547 | 3/1982 | Minisci et al. | 560/204 |
| 4,360,691 | 11/1982 | Perrin | 560/204 X |

FOREIGN PATENT DOCUMENTS 281334 10/1978 Fed. Rep. of Germany .

OTHER PUBLICATIONS

L. P. Vinogradova et al., Chem. Abst., 56, 338, (1962).
K. Ruhl, L. fur Naturf., (Journal of Natural Science), 4B, 199, (1949).
G. Kommpa, Ann. 368, 126, (1909).
W. T. Smith and G. L. McLeod, Org. Synthesis 31, 40, (1951).
J. Walker and J. K. Wood, J. Chem. Soc., 89, 598, (1906).

Primary Examiner—Natalie Trousof
Assistant Examiner—Vera C. Clarke
Attorney, Agent, or Firm—Fisher, Christen & Sabol

[57] ABSTRACT

Process for the production of 3,3-dimethylglutaric acid or its esters from dimedone. Dimedone is converted with ozone into an ozone-addition product. The latter is converted by hydrolysis into 3,3-dimethylglutaric acid or by alcoholysis into one of its esters.

8 Claims, No Drawings

PROCESS FOR THE PRODUCTION OF 3,3-DIMETHYLGLUTARIC ACID OR ITS ESTERS

BACKGROUND OF THE INVENTION

1. Field Of The Invention

The invention relates to a process for the production of 3,3-dimethylglutaric acid and its esters from dimedone.

2. Prior Art

Various methods for the production of 3,3-dimethylglutaric acid are known from the literature. Thus, according to G. Comppa, Ann. 368, 126 (1909), W. T. Smith and G. L. McLeod, Org. Synthesis 31, 40, (1951), and J. Walker and J. K. Wood, J. Chem. Soc., 89, 598, (19063,3-dimethylglutaric acid is obtained by oxidation of dimedone (i.e., 5,5-dimethyl-1,3-cyclohexanedione) with sodium hypochlorite. L. P. Vinogradova et al., Chem. Abst., 56, 338, (1962), and K. Ruhl, L. fur Naturf. (Journal for Natural Science) 4B, 199, (1949), describe the oxidation of dimedone with hydrogen peroxide. Both processes have major disadvantages. The first process requires a large volume of hypochlorite solution and produces among other things, a large amount of organic waste; and in the case of the other process, the large consumption of expensive hydrogen peroxide is an impediment which is a serious disadvantage.

BROAD DESCRIPTION OF THE INVENTION

It is an object of the invention to provide a process for producing 3,3-dimethylglutaric acid and its esters from dimedone. Another object of the invention is to provide a process for producing 3,3-dimethylglutaric acid, starting out from a relatively cheap educt, in a simple manner and with high purity, so that no subsequent expensive purification processes are necessary. Other objects and advantages of the invention are set out herein or are obvious herefrom to one ordinarily skilled in the art.

The objects and advantages of the invention are achieved by the process and composition of the invention.

The invention involves a process for the production of 3,3-dimethylglutaric acid or one of its esters from dimedone. In the process dimedone is converted with ozone into an ozone addition product and the latter is converted by hydrolysis into the 3,3-dimethylglutaric acid or by alcoholysis into one of its esters.

Whenever 3,3-dimethylglutaric acid is sought as the synthesized product, the hydrolysis of the ozone-addition product is effectively carried out with the help of hot water, preferably boiling water.

Whenever the end product is to be a 3,3-dimethylglutaric acid ester, the splitting of the ozone-addition product is carried out with the simultaneous formation of the ester using an alcohol in the presence of a mineral acid. The alcohols used must agree with the alcohol part of the desired ester.

3,3-dimethylglutaric acid and its esters are intermediates in the production of pesticides (German OS No. 28 13 341) and are suitable as additives to lubricating oil (U.S. Pat. No. 2,971,915).

By way of summary, 3,3-dimethylglutaric acid is obtained from dimedone (which can be that which originates, without isolation, from the conversion of isophorone by way of 3,3-dimethyl-5-oxo-hexanoic acid methyl ester) by ozone addition and subsequent hydrolysis. The invention process is simple, and produces a product of high purity, which means that no subsequent expensive purification process is required.

DETAILED DESCRIPTION OF THE INVENTION

As used herein, all parts, percentages ratios and proportions are on a weight basis unless otherwise stated herein or otherwise obvious herefrom to one ordinarily skilled in the art.

The ozonolysis is effectively carried out at a temperature of $-80°$ to $+40°$ C., preferably at $-10°$ to $+20°$ C. The reaction time depends mainly on the performance of the ozone generator. Medium reaction time lies at about 0.5 to 5 hours.

It is also possible to use a dimedone as the starting material which is produced by cyclization from 3,3-dimethyl-5-oxo-hexanoic acid ester with sodium alcoholates and thus is not presently isolated in an alcoholic solution. Such 3,3-dimethyl-5-oxo-hexanoic acid ester can be produced from isophorone. (Isophorone is also termed isoacetophorone and 3,5,5-tri-methyl-2-cyclohexen-1-one.) The isophorone can be converted, for example, by treatment with ozone into an ozone-addition product and the acid is formed from the latter by hydrolysis.

Whenever the process starts with isolated dimedone, and a 3,3-dimethylglutaric acid diester is the desired product, then their solvents can also be used instead of an alcohol with the restriction that such solvent must not react with alcohol or ester under the conditions of the reaction. Suitable solvents are esters, such as, ethylacetate, chlorohydrocarbons, such as, methylene chloride, or hydrocarbons, preferably toluene and hexane. In the case of such the use of such solvent, it is then necessary after formation of the dimedone-ozone addition product to add the suitable alcohol.

The alcohols used to produce the esters preferably have 1 to 6 carbon atoms; the ester moieties preferably have 1 to 6 carbon atoms. Examples of useful alcohols are methanol, ethanol, propanol, isopropanol, butanol, isobutanol, pentanol and hexanol.

Whenever 3,3-dimethylglutaric acid is desired as the reaction product, then after completion of the ozonolysis and the succeeding hydrolysis, the reaction mixture is cooled to ambient temperature and the product is extracted with ether and the latter is subsequently evaporated. After drying one obtains white crystalline, crude 3,3-dimethylglutaric acid having a purity of 85 percent. By washing with a little toluene and hexane the purity is raised to 98 percent.

Small quantities of the 3,3-dimethylglutaric monomethyl ester can be isolated from the filtrate, which in turn can be recycled back into the process. If one takes the reusability of this byproduct into consideration, then the selectivity amounts to 90 to 91 percent.

Whenever an ester of the 3,3-dimethlglutaric acid is desired as the reaction product, then the ozone-addition product is converted with an alcohol and in the presence of a catalytic quantity of a mineral acid (such as, HCl and preferably $H_2SO_4$). The addition of the alcohol is accomplished at the latest after formation of the ozone-addition product.

After alcoholysis is completed, the reaction solution is cooled down to ambient temperature with a base (preferably caustic soda, i.e., NaOH), dissolved in an alcohol, neutralized and separated by distillation.

The diesters of the 3,3-dimethylglutaric acid obtained have a purity of over 97 percent.

EXAMPLE 1

4.8 g of sodium metallic sodium was dissolved in 100 ml of anhydrous methanol and this was heated to reflux. To this, 30.0 g of 3,3-dimethyl-5-oxo-hexanoic acid methyl ester, which originated from the conversion of isophorone with ozone and which had a content of 98.1 percent, was added drop by drop over the course of 0.5 hours. Subsequently, the solution was refluxed for another 2 hours. After cooling down, the solution was acidified with concentrated sulfuric acid to pH 2. The precipitated sodium sulfate was filtered out; the filtration could be facilitated by the addition of 2.0 g of a filtration auxiliary (for example, Clarcel Type Disc 3). The filter residue was washed again with 100 g of methanol. The resultant solution contained (according to analytic determination) 22.64 g of dimedone. The solution of dimedone in methanol was cooled to $-2°$ to $0°$ C. Subsequently a stream of about 4 percent of ozone in oxygen was introduced into the solution up to its saturation for the purpose of producing an ozone-addition product.

After ozonolysis was completed, the solution of the developed ozone-addition product was added drop by drop into 200 ml of boiling water and was heated to reflux temperature during 3 hours. After the hydrolysis, the entire product was cooled down to ambient temperature and extracted three times with 80 ml of ether. The ether was cupelled from the extract by evaporation. The crystals which had formed of the crude 3,3-dimetylgluaric acid were dried. The purity was 85 percent (according to GC).

Subsequently, the crude 3,3-dimethylglutaric acid was washed again on a filter with 20 ml of toluene and 20 ml of hexane. As a result of that it was possible to increase the purity of the product to 98 percent. Consequently, 21.83 g of white crystals of 3,3-dimethylglutaric acid at 98.0 percent were obtained after the drying step. The crystals had a melting point of 100.5° to 101.5° C. The yield, calculated on the basis of the amount of dimedone, was 82.7 percent and, on the basis of the amount of 3,3-dimethyl-5-oxo-hexanoic acid methyl ester, was 78.1 percent.

As a byproduct, 2.28 g of 3,3-dimethylglutaric monomethyl ester was obtained and could be used again in the synthesis. If such byproduct is taken into consideration then the selectivity of the reaction, related to the converted 3,3-dimethyl-5-oxo-hexanoic methyl ester, was 85.5 percent.

EXAMPLE 2

A solution, produced from 14.0 g of solid dimedone and 110 g of methanol, was ozonolized as in Example 1. After the ozonolysis was completed, 0.92 g of concentrated sulfuric acid was added slowly to the developed ozone-addition product. The acid solution was boiled under reflux for 3 hours. After the alcoholysis, the solution was cooled to ambient temperature and neutralized with sodium hydroxide. The methanol was distilled off and subsequently the 3,3-dimethylglutaric dimethyl ester was isolated by vacuum distillation (90° C/14 mbar).

16.8 g of a colorless fluid was obtained (which according to gas chromotography) contained 98.0 percent of 3,3-dimethylglutaric acid dimethyl ester. This corresponds to a yield of 87.6 percent, calculated on the basis of the amount of dimedone used.

EXAMPLE 3

A solution, produced from 14.0 of solid dimedone, 55.0 g of glacial acetic acid and 55.0 g of ethylacetate, was ozonolysed as in Example 1, and then hydrolyzed by adding it drop by drop into 200.0 g of boiling water. The hydrolozate was evaporated to dryness. The crystals formed of the crude 3,3-dimethylglutaric acid were washed with 20 ml of toluene and 20 ml of hexane on a filter. As result of the washings, the purity of the product was increased to 98.1 percent. After the drying, 13.9 g of white crystals of 3,3-dimethylglutaric acid was obtained (melting point 101° to 102° C.), which correspond to 13.6 g of 100 percent 3,3-dimethylglutaric acid. The yield, calculated on the amount of dimedone used, was 85.0 percent.

What is claimed is:

1. Process for the production of 3,3-dimethylglutaric acid or its methyl ester, ethyl ester, propyl ester, isopropyl ester, butyl ester, isobutyl ester, pentyl ester or hexyl ester from dimedone comprising converting dimedone with ozone into an ozone-addition product and converting the ozone-addition product by hydrolysis into the 3,3-dimethylglutaric acid or by alcoholysis into one of its esters.

2. Process as claimed in claim 1 wherein the hydrolysis is carried out in hot water.

3. Process as claimed in claim 1 wherein the hydrolysis is carried out in boiling water.

4. Process as claimed in claim 1 wherein the ozone-addition product is converted by treatment with methanol, ethanol, propanol, isopropanol, butanol, isobutanol, pentanol or hexanol into a 3,3-dimethylglutaric acid ester.

5. Process as claimed in claim 4 wherein treatment is done with methanol.

6. Process as claimed in claim 1 wherein the ozonolysis is carried out at a temperature of 80° to +40° C.

7. Process as claimed in claim 1 wherein the ozonolysis is carried out at a temperature of $-10°$ to $+20°$ C.

8. Process for the production of 3,3-dimethylglutaric acid or its methyl ester, ethyl ester, propyl ester, isopropyl ester, butyl ester, isobutyl ester, pentyl ester or hexyl ester, comprising cyclizing a 3,3-dimethyl-5-oxohexonic ester with sodium alcoholate into dimedone, and converting the dimedone with ozone into a ozone-addition product and converting the ozone-addition product by hydrolysis into the 3,3-dimethylglutaric acid or by alcoholysis into one of its esters.

* * * * *